(12) United States Patent
Eda et al.

(10) Patent No.: US 7,233,819 B2
(45) Date of Patent: Jun. 19, 2007

(54) METHOD FOR MAPPING HIGHER BRAIN FUNCTION AND HEADGEAR FOR MAPPING HIGHER BRAIN FUNCTION

(75) Inventors: Hideo Eda, Tokyo (JP); Tsutomu Murata, Tokyo (JP); Akira Takatsuki, Tokyo (JP)

(73) Assignee: National Institute of Information and Communications Technology (JP)

( * ) Notice: Subject to any disclaimer, the term of this patent is extended or adjusted under 35 U.S.C. 154(b) by 664 days.

(21) Appl. No.: 10/679,424

(22) Filed: Oct. 7, 2003

(65) Prior Publication Data

US 2005/0177041 A1 Aug. 11, 2005

(30) Foreign Application Priority Data

Mar. 20, 2003 (JP) .......................... P2003-077809

(51) Int. Cl.
*A61B 5/055* (2006.01)
*A61B 6/00* (2006.01)

(52) U.S. Cl. .................. 600/411; 600/426; 600/473; 264/222

(58) Field of Classification Search ............. 600/410, 600/411, 414, 426, 473, 475–478; 264/219, 264/220, 222
See application file for complete search history.

(56) References Cited

U.S. PATENT DOCUMENTS 6,374,135 B1 4/2002 Bucholz
6,996,261 B2 * 2/2006 deCharms .................. 382/131

FOREIGN PATENT DOCUMENTS

| GB | 2 311 854 A | 10/1997 |
|---|---|---|
| JP | 2003 93390 A | * 4/2003 |
| JP | 2003-322612 A | 11/2003 |
| WO | WO 98/27865 A | 7/1998 |

OTHER PUBLICATIONS

Marcus E. Raichle, "A Brief History of Human Functional Brain Mapping," *Brain Mapping, The Systems*, Academic Press, 2000, pp. 64-65.
C. Hirth, "Towards Brain Mapping Compining Near-Infrared Spectroscopy and High Resolution 3D MRI," *Advances in Experimental Medicine and Biology*, Spring St., New York, 1997, vol. 413, pp. 139-147.

* cited by examiner

*Primary Examiner*—Ruth S. Smith
(74) *Attorney, Agent, or Firm*—Banner & Witcoff, Ltd.

(57) ABSTRACT

A method for mapping higher brain function comprises an fMRI mapping step S1 to map a brain function of the subject TP by fMRI, a head portion structural image acquisition step S3 to acquire a head portion structural image IMGs by an MRI system in a state that a headgear HC having a marker is mounted on the head portion of the subject TP, a three-dimensional image combining step S4 to create a three-dimensionally combined image IMGfs by combining the head portion structural image IMGs and the brain functional image IMGf obtained by the fMRI mapping step S1, an optical probe mounting step S5 to specify positions on the headgear HC where optical probes PR1, PR2 are mounted based on the three-dimensionally combined image IMGfs and to mount the optical probes PR1, PR2 at the specified positions and an NIRS measuring step S6 to conduct the NIRS by a NIRS method in a state that the headgear HC loaded with the optical probes PR1, PR2 is mounted on the head portion of the subject TP.

10 Claims, 9 Drawing Sheets

METHOD FOR MAPPING HIGHER BRAIN FUNCTION AND HEADGEAR FOR MAPPING HIGHER BRAIN FUNCTION

CROSS REFERENCE TO RELATED APPLICATIONS

This application is based upon and claims the benefit of priority from the prior Japan Patent Application No. P2003-77809, filed Mar. 20, 2003, the entire contents of which are incorporated herein by reference.

BACKGROUND OF THE INVENTION AND RELATED ART STATEMENT

This invention relates to a method for mapping higher brain function to measure higher brain function with accuracy and to a headgear used in the method.

Recently a method for measuring brain activity in a noninvasive manner and for analyzing brain function has been conceived and various devices or systems for the method have been developed. For example, fMRI (functional magnetic resonance imaging) and NIRS (near-infrared spectroscopy) are representative examples of a method for mapping brain function. See, for example, Raichle, Marcus E., "A Brief History of Human Functional Brain Mapping" *Brain Mapping, The Systems,* Academic Press, 2000, p. 64–65.

The fMRI is primarily based on a BOLD effect that measures a change of signal intensity of MRI based on a fluctuation of deoxygenated hemoglobin (Deoxy-Hb) value of blood in a brain and images it so as to monitor a local brain activity. The fMRI specifies an activated portion from a brain functional image obtained with an extremely high space resolution such as a mm order. In the meantime, the NIRS is to irradiate near-infrared pulse light of a predetermined wavelength on a head portion of a subject through a probe for irradiation (optical fiber) and to detect the corresponding near-infrared light diffused from the brain with a high time resolution such as several tens of milliseconds through a probe for detection (optical fiber). More specifically, oxygenated hemoglobin concentration, deoxygenated hemoglobin concentration and a total hemoglobin concentration of blood in a brain are measured by transmitting near-infrared light through a probe connected to a holder mounted on the head portion of the subject by making use of the near-infrared light having a wavelength that penetrates a skin tissue or a bone tissue and that is absorbed by oxygenated hemoglobin or deoxygenated hemoglobin of the blood, and a brain activity of the subject while exercising or in a stationary state is measured or imaged with a high time resolution by means of a blood circulation kinetics change in the brain of the subject derived from a diachronic concentration change. See, for example. Japanese Patent Specification 2002-128107.

The fMRI is superior in a space resolution as mentioned above, but inferior in a time resolution since, at most only a piece of an image can be imaged in a few seconds. In addition, in order to conduct the fMRI a subject is encased in an almost blocked system and a brain activity of the subject is measured in the system, which makes it difficult to measure the brain activity of the subject, for example, during an exercise with moving his or her body. Further, nowadays the BOLD effect itself is the fundamental principle of the fMRI under review. On the other hand, the NIRS is, as mentioned above, superior in a time resolution and the subject can be monitored in either an unconstrained condition or a constrained condition, however, the monitoring depends on a position where a probe is mounted, thereby performing a low space resolution of a few cm order at most.

Based on the above-mentioned problem, it might be assumed mistakenly that merely combining the fMRI and the NIRS, in other words, just checking both results of the fMRI and the NIRS, covers each weak point and a result of measuring brain function is superior both in the time resolution and the space resolution. However, since it is unclear that results of the fMRI and the NIRS always correspond with each other, merely combining both of the fMRI and the NIRS does not produce an agreeable result.

In order to solve the above problems the present claimed invention mainly intends to provide a method for mapping higher brain function wherein advantages of the fMRI and the NIRS can be demonstrated and the results of both methods can be compliant with each other definitely and to provide a suitable headgear used for the method.

SUMMARY OF THE INVENTION

The method for mapping higher brain function in accordance with the present claimed invention is a method for mapping higher brain function to map a higher brain function while a body of a subject is in a resting state or in a predetermined active state and is characterized by comprising an fMRI mapping step to map a brain function of the subject by functional magnetic resonance imaging, a head portion structural image acquisition step to acquire a head portion structural image of the subject by the magnetic resonance imaging in a state that a headgear having a predetermined marker is mounted on the head portion of the subject, a three-dimensional image combining step to create a three-dimensionally combined image showing the brain function and the head portion structure of the subject simultaneously by three-dimensionally combining the brain functional image obtained by the fMRI mapping step and the head portion structural image, an optical probe mounting step to specify a position on the headgear where an optical probe that is used for near-infrared spectroscopy is mounted based on the three-dimensionally combined image and to mount the optical probe at the specified position, and an NIRS measuring step to map the brain function of the subject by the near-infrared spectroscopy in a state that the headgear loaded with the optical probe is mounted on the head portion of the subject.

More specifically, in the fMRI mapping step, first a general activated portion of the brain when a predetermined stimulus is applied to the subject is specified based on a brain functional image obtained by the fMRI. In the head portion structural image acquisition step that is conducted prior to or after the fMRI mapping step, a head portion structural image of the subject wearing the headgear, namely, an image on which whole of the head portion of the subject and a shape of the brain is displayed together with the markers is obtained by the MRI. In the three-dimensional image combining step, the brain functional image and the head portion structural image are combined into an image by a computer processing and the activated portion is displayed on the head portion structural image. This makes it possible to specify the marker corresponding to the activated portion with a highly accurate space resolution. In the optical probe mounting step, an optical probe is mounted near the specified marker. In the NIRS measuring step, a diachronic change of hemoglobin (total amount of Hb), oxygenated hemoglobin (oxy-Hb) and deoxygenated hemoglobin (deoxy-Hb) in blood of each activated portion are measured with a highly accurate time resolution. As a result, an activated portion of the brain specified by the fMRI and a diachronic change of a brain function based on a change of Hb in blood at the activated portion by the NIRS can be homologized certainly, thereby to fully utilize merits of both of the fMRI and the NIRS.

Especially, during the optical probe mounting step it is preferable that a marker corresponding to an activated portion of the brain determined based on the brain functional image included in the three-dimensionally combined image is specified from the markers on the headgear determined based on the head portion structural image included in the three-dimensionally combined image and an optical probe for irradiation of near-infrared light and an optical probe for detection of the near-infrared light diffused from the brain are mounted in pairs near the specified marker on the headgear. In this case, it is suitable that the optical probe for irradiation and the optical probe for detection are arranged apart by a predetermined distance across a corresponding marker. Further, a distance between the optical probe for irradiation and the optical probe for detection or a direction of arranging the optical probe for irradiation and the optical probe for detection may be determined based on a shape of the activated portion of the brain, a physical condition of the headgear, a positional relationship with other adjacent optical probe or a theoretical analysis result of brain optical propagation.

It is necessary for this method to make a headgear. In order to make the headgear it is preferable the method further comprises a headgear manufacturing step to manufacture the headgear and the headgear for the subject's exclusive use tailored to each subject is manufactured during the headgear manufacturing step. More specifically, since a shape of a head portion and brain varies depending on each subject, a generalized headgear is not suitable for the purpose of accuracy. Then a custom-made headgear that fits for each subject makes it possible to specify an activated portion of the brain of the subject and to measure an Hb change in blood with an extreme accuracy. In order to further improve an accuracy of measurement by the NIRS measuring step at the activated portion of the brain specified by the fMRI mapping step it is preferable that a plurality of the markers are evenly embedded at predetermined intervals into the headgear during the headgear manufacturing step. As a concrete headgear manufacturing step represented is that the head portion of the subject is covered with a flexible film such as a kitchen wrap film, then a molding material is applied on the film in a flexible condition so as to make the headgear molded into a form of the head portion of the subject and the markers are embedded into the molding material before the moldings material is cured during the headgear manufacturing step. In accordance with the arrangement, it is possible to avoid double labor of making a plaster cast of a head portion of a subject and then molding a headgear made of resin by making use of the plaster cast, thereby to manufacture the headgear with ease in a short time. A kneaded dental rubber elastic impression material of binary kneaded-type or a heat distortion resin material can be applied as an impression material.

In the above-mentioned method for mapping higher brain function in accordance with the present claimed invention, the headgear is extremely important. More specifically the headgear in accordance with the present claimed invention is characterized by comprising a gear body formed into a shape of the head portion of the subject with a molding material of either a kneaded dental rubber elastic impression material of binary kneaded-type or a heat distortion resin material attached in a flexible condition to the head portion of the subject and then cured and a plurality of makers embedded at predetermined intervals into the molding material prior to curing. A soft molding material may be independently used if a certain degree (for example, more than 5 mm) of thickness is secured.

Especially in the head portion structural image acquisition step, if the headgear is misaligned between a time of taking a head portion structural image with a marker included and the NIRS measuring step, an undesired effect will be produced on a result of the measurement. In order to prevent this problem with ease, it is preferable that a positioning portion that corresponds to either one or both of a nose and an ear of the subject is formed with the molding material before the molding material is cured.

The maker is preferably an adipose sphere, for example, a fat-soluble granular substance that can be reflected in the structural image taken by the MRI and easily available as well. As an easily available marker represented is a tablet of vitamin D.

Further, if a molding material is directly applied to the head portion of the subject, the molding material is difficult to be removed from the head portion of the subject after cured. However, the molding material is required to copy a shape of the head portion of the subject precisely as much as possible. In order to meet both requirements it is effective that the gear body is formed by applying the molding material on a flexible film such as a kitchen wrap film that is attached to the head portion of the subject in advance.

DETAILED DESCRIPTION OF THE PREFERRED EMBODIMENTS

An embodiment of the present claimed invention will be described in detail with reference to the accompanying drawings.

Figure 1:
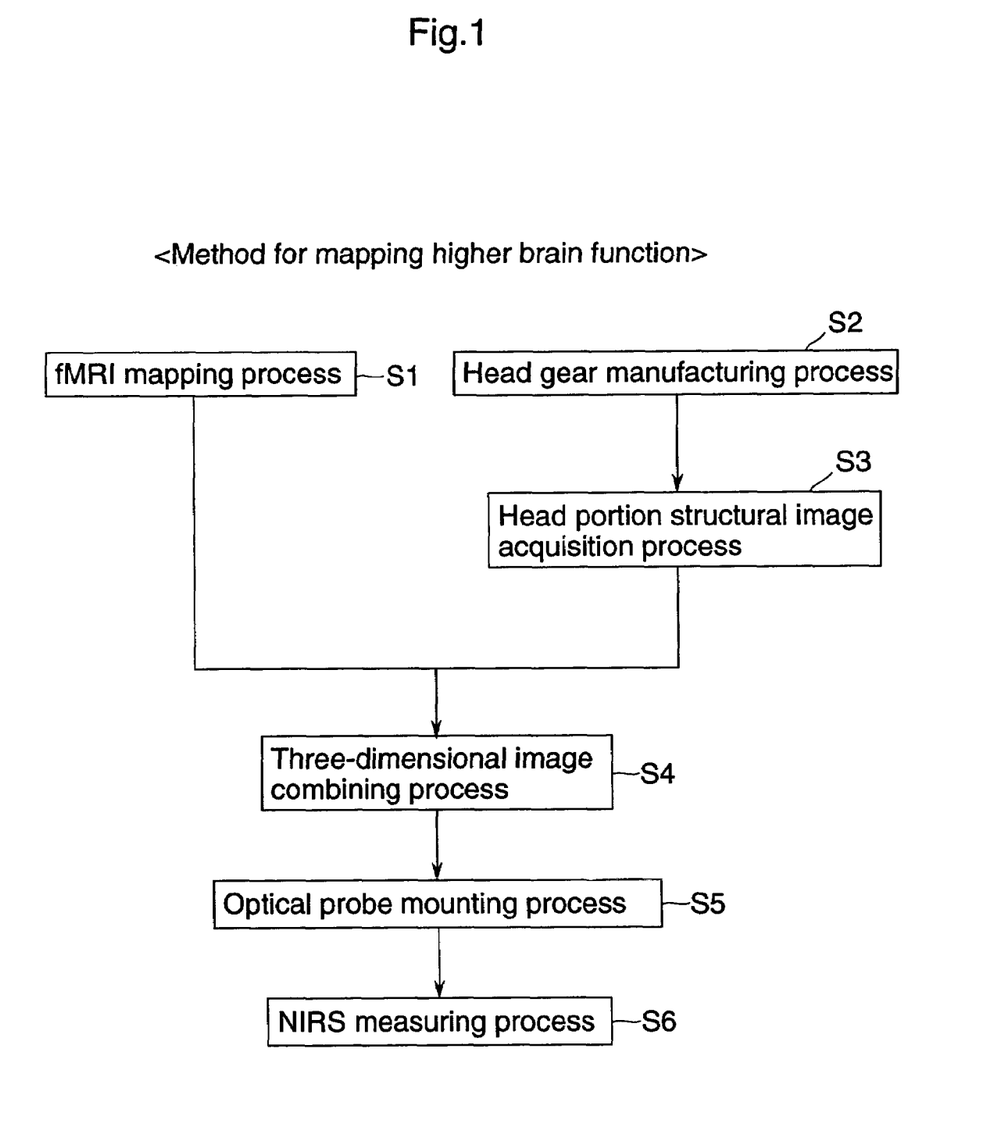
FIG. 1 is a flow chart showing each step of a method for mapping higher brain function in accordance with the present claimed invention.

This embodiment is a method for mapping higher brain function appropriately combined an fMRI with an NIRS and the method comprises, as shown in FIG. 1, an fMRI mapping step S1, a headgear manufacturing step S2, a head portion structural image acquisition step S3, a three-dimensional image combining step S4, an optical probe mounting step S5 and an NIRS measuring step S6. A headgear HC used for the method for mapping higher brain function in accordance with the embodiment will also be explained.

Figure 2:
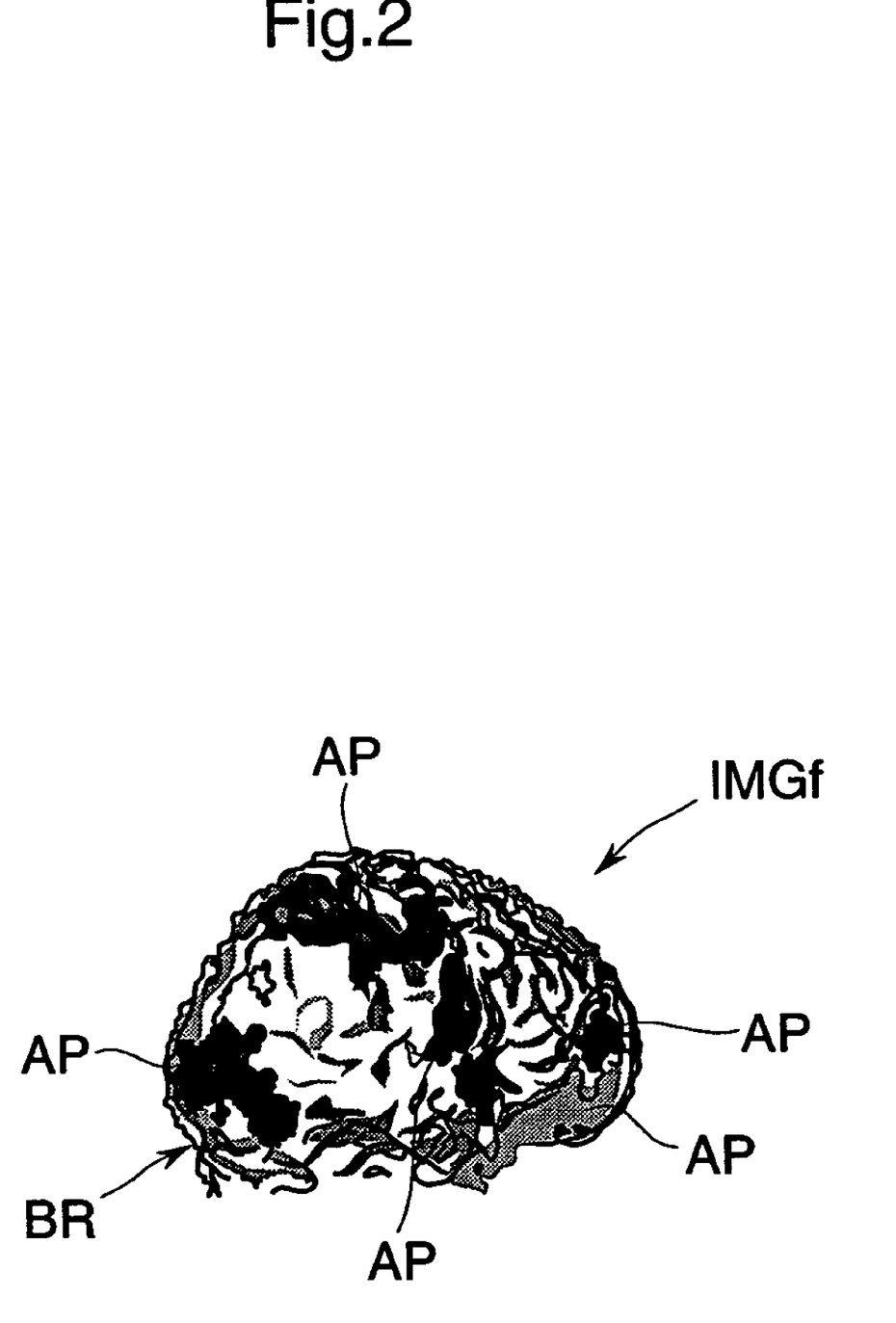
FIG. 2 is a view showing an example of a brain functional image obtained from an fMRI mapping step in accordance with the embodiment.

In the fMRI mapping step S1, a predetermined task is performed by a subject TP inside an MRI system and an image of an active state of a whole brain BR of the subject TP is taken like the ordinary fMRI mapping method. FIG. 2 is a brain functional image IMGf obtained as a result of a test "binocular rivalry" wherein different images are shown to each of right and left eyes of the subject TP respectively. Since a body of the subject TP is fixed in the MRI system, the subject TP puts on a pair of glasses GR (refer to FIG. 7) in order to show the different image to each eye. The brain functional image IMGf is obtained as a three-dimensional image. FIG. 2 shows a state of the brain BR of the subject TP viewed from a right side. A gray-scaled portion in the brain functional image IMGf shown in FIG. 2 is an activated portion AP of the brain BR. A portion where the gray is deeper shows that the brain BR activity is higher. More specifically, a rough position of the activated portion AP of the brain BR activated by a predetermined stimulus can be obtained in the fMRI mapping step S1. In this case for displaying the brain functional image IMGf, a denoted area of the activated portion AP can be varied by determining a threshold at discretion, wherein the bigger a statistical screening value (p value) used as a threshold is, the smaller a denoted area of the activated portion AP becomes, conversely the smaller the p value is, the bigger the denoted area of the activated portion AP becomes.

Figure 3:
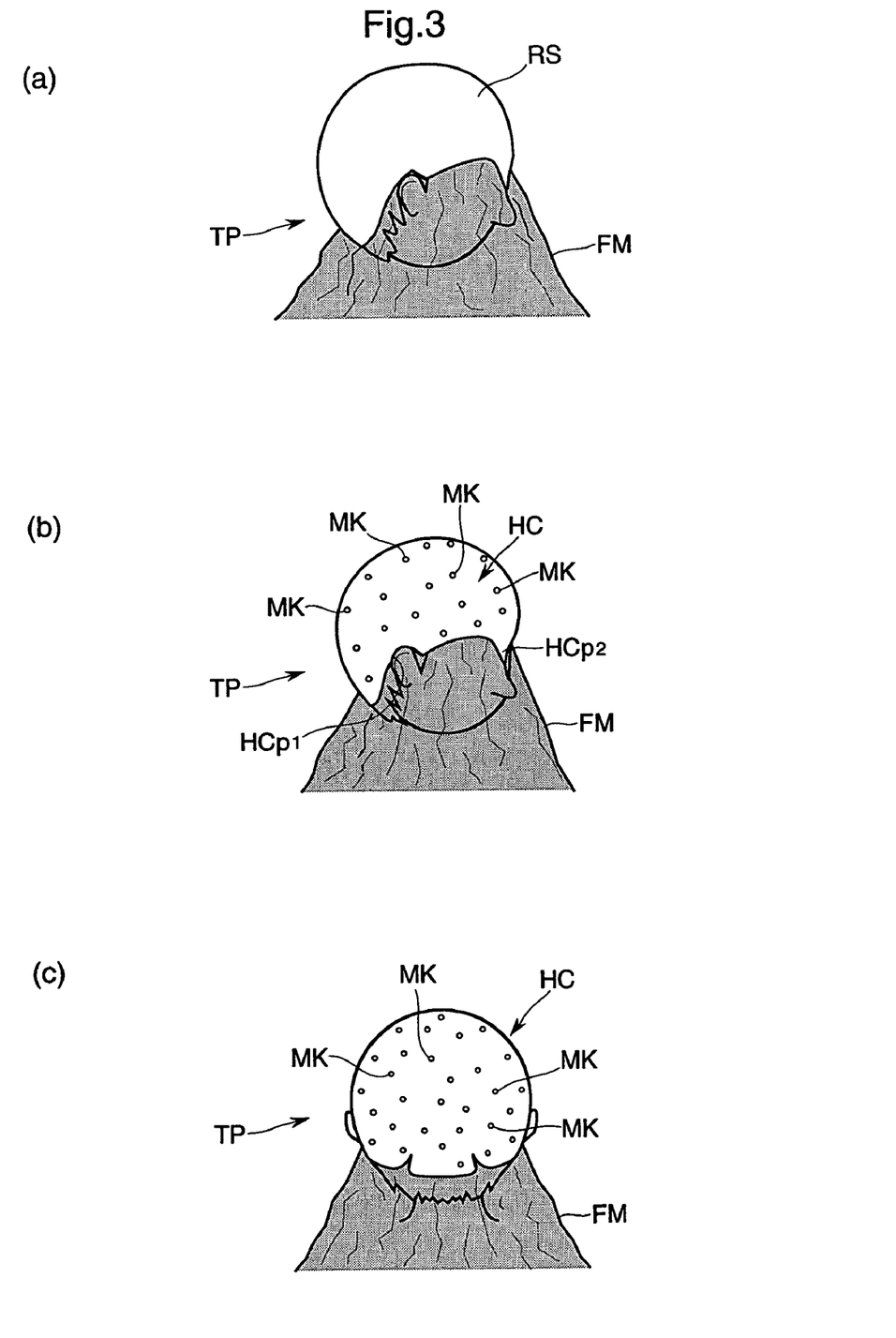
FIG. 3 is a view showing a step of manufacturing a headgear in accordance with the embodiment.

In the headgear manufacturing step S2, the headgear HC to cover the head portion of the subject TP in the NIRS measuring step S6 is manufactured. A concrete explanation will be given with referring to FIG. 3. First, as shown in FIG. 3(a), the head portion of the subject TP is covered with a thin and flexible resin film FM (for example, a kitchen wrap film). Then a molding material RS kneaded with a dental rubber elastic impression material of binary kneaded-type is applied to the resin film FM over the head portion of the subject TP with a thickness of more than about 5 mm and placed for a while until it cures so as to form a custom-made headgear HC that fits a shape of the head portion of the subject TP. In other word, the cured molding material RS will make the headgear HC in itself. In this case, positioning portions HCp1, HCp2 are formed with the molding material RS at positions across each ear of the subject TP back and forth and at a position surrounding an upper part of a nose of the subject TP in order to provide positioning appropriately when the subject TP puts on this headgear HC later. Prior to curing the molding material RS, as shown in FIG. 3(b) and FIG. 3(c), grainy markers MK are embedded into the headgear HC. Since an adipose sphere is preferable as the marker MK, an over-the-counter vitamin D tablet (fat-soluble material) is used. The marker MK is embedded into the headgear HC with penetrating a thickness thereof and arranged evenly across the board of the headgear HC as much as possible.

Figure 4:
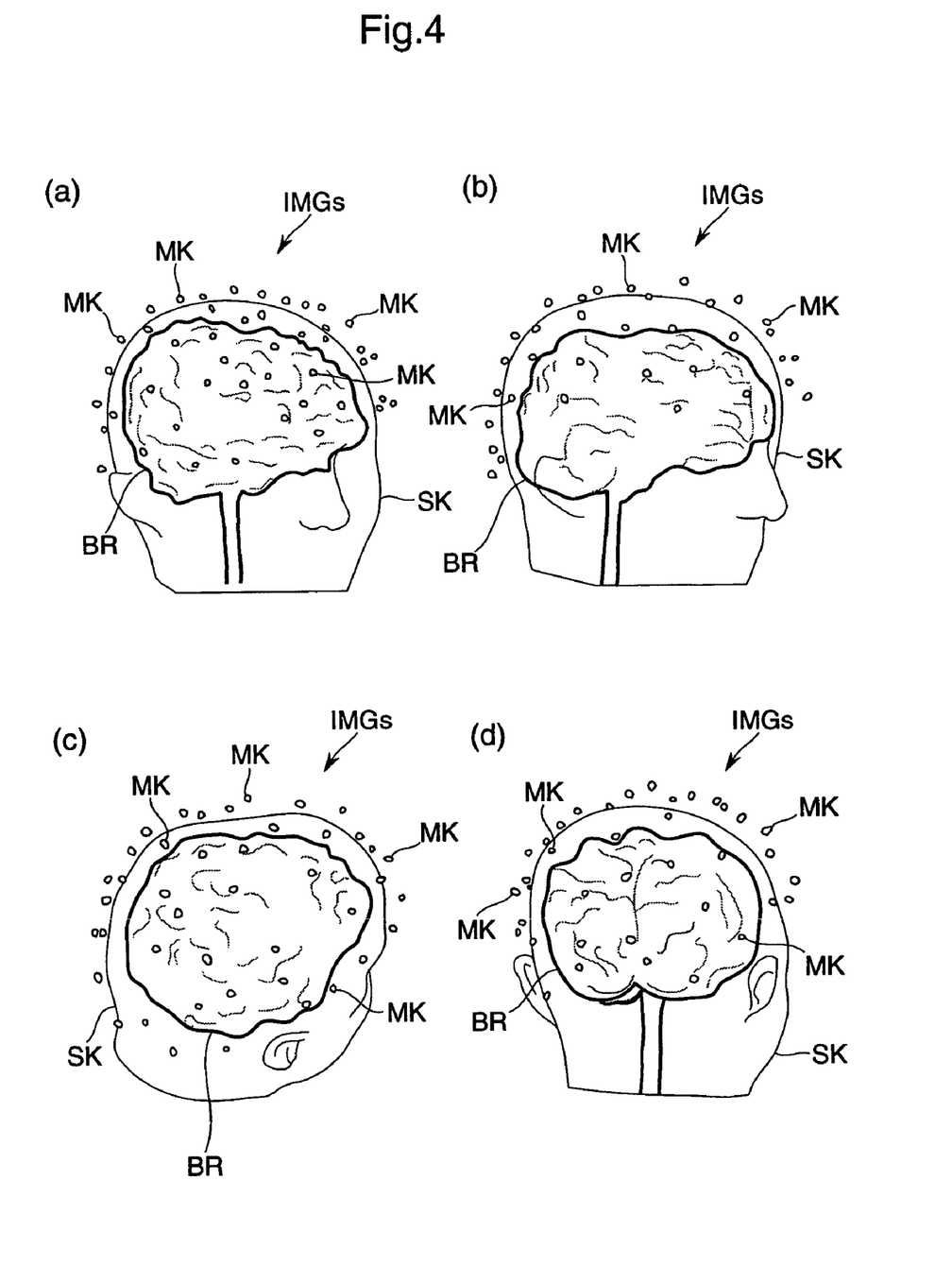
FIG. 4 is a view showing an example of a head portion structural image obtained by a head portion structural image acquisition step in accordance with the embodiment.

In the head portion structural image acquisition step S3, an image of the head portion of the subject TP is taken so as to acquire a head portion structural image IMGs in a condition that the head portion of the subject TP is covered with the headgear HC manufactured in the above headgear manufacturing step S2. FIG. 4 shows the head portion structural image IMGs obtained in the step S3. FIG. 4(a) is a three-dimensional view of the head portion of the subject TP viewed from diagonally right and front, FIG. 4(b) is a three-dimensional view of the head portion of the subject TP viewed from further diagonally right and front than FIG. 4(a), FIG. 4(c) is a three-dimensional view of the head portion of the subject TP viewed from diagonally right behind and above and FIG. 4(d) is a three-dimensional view of the head portion of the subject TP viewed from the back. Each view shows a state of a single head portion structural image IMGs viewed from three-dimensionally different directions. A scalp SK, the brain BR and the markers MK of the head portion of the subject TP are shown in each head portion structural image IMGs. Especially, the markers MK are shown in a slightly floated state above the scalp SK.

Figure 5:
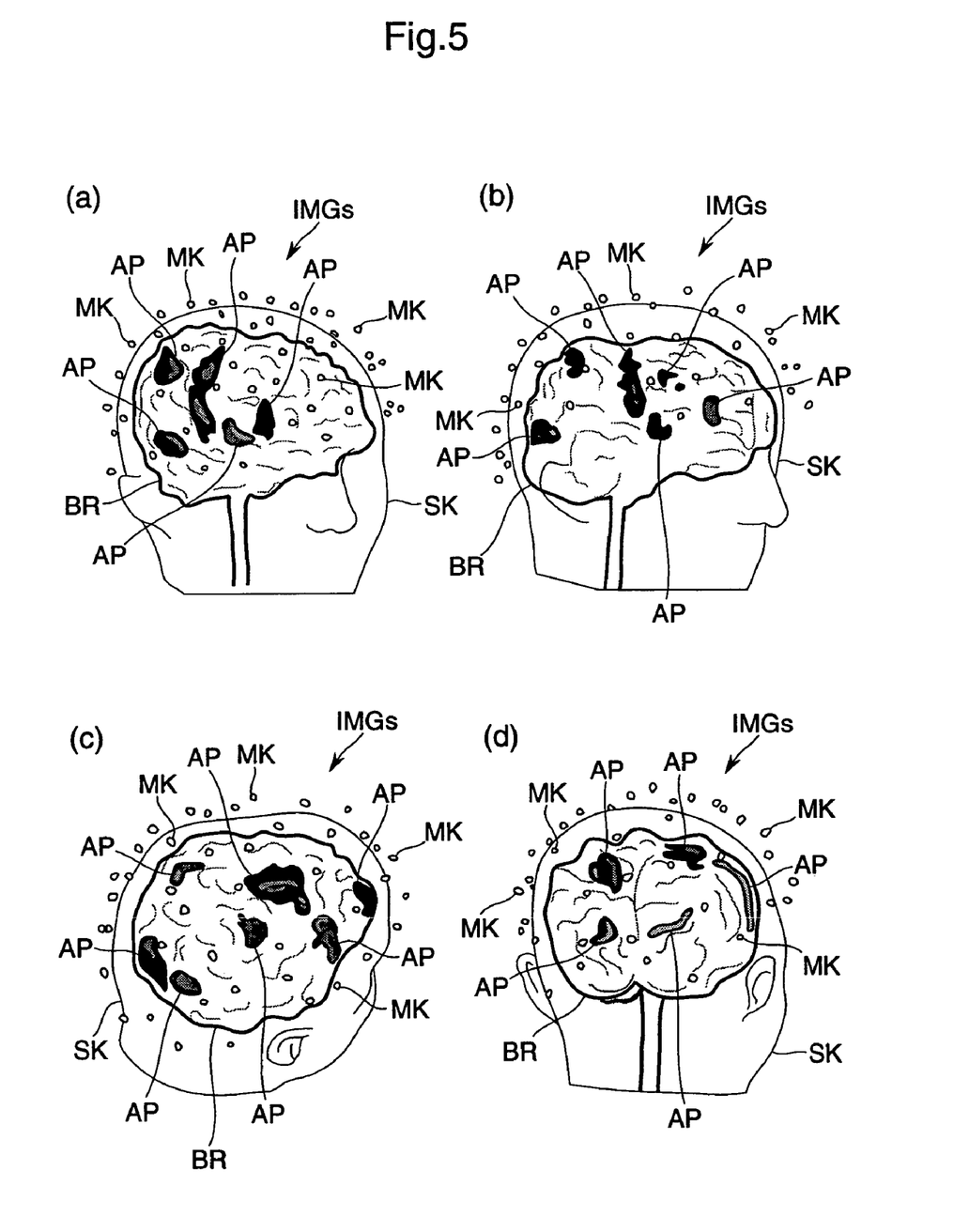
FIG. 5 is a view showing an example of three-dimensionally combined image combined with the brain functional image and the head portion structural image in accordance with the embodiment.

In the three-dimensional image combining step S4, the brain functional image IMGf obtained in the above-mentioned fMRI mapping step S1 and the head portion structural image IMGs obtained in the above-mentioned head portion structural image acquisition step S3 are combined so as to create a three-dimensionally combined image IMGfs that shows a brain function and a structure together. More specifically, since both the brain functional image IMGf and the head portion structural image IMGs include an image of the brain of the same subject TP, one of the images IMGs, IMGf is fixed based on a shape of the brain and other image is moved so as to coincide both of the brain images. This step can be done with ease by making use of, for example, a multi-purpose statistical parametric mapping software. (an example: Statistical Parametric Mapping SPM by London University) The images IMGf, IMGs whose brain shapes are coincided are overlapped by making use of a rendering software (for example, Analyze software) and then the overlapped images IMGf, IMGs including the scalp SK and the markers MK are processed with a rendering processing so as to obtain a three-dimensionally combined image IMGfs. FIG. 5(a) through FIG. 5(d) show the three-dimensionally combined image IMGfs of the subject TP corresponding to the head portion structural image IMGs shown in FIG. 4(a) through FIG. 4(d). More specifically, a structure of the head portion, (the brain BR, the scalp SK) the markers MK on the headgear HC and the activated portion AP of the brain BR of the subject TP are expressed on the same three-dimensionally combined image IMGfs.

Figure 6:
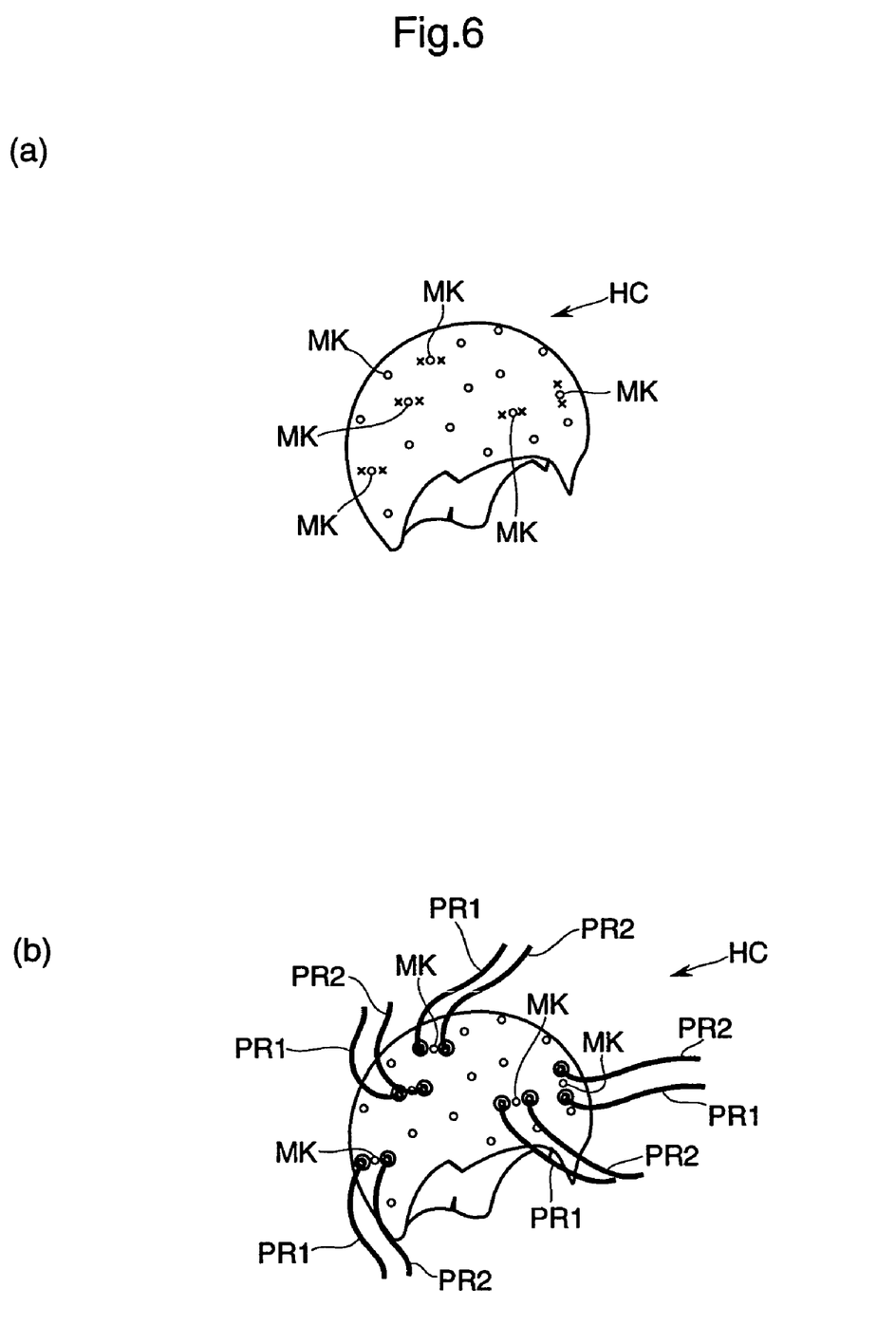
FIG. 6 is a view showing an optical probe mounting step in accordance with the embodiment.

In the optical probe mounting step S5, a marker MK nearest to the activated portion AP of the brain BR is selected and two marks (x mark in FIG. 6(a)) are put across the marker MK as shown in FIG. 6(a) based on the three-dimensionally combined image IMGfs obtained by the three-dimensional image combining step S4. And then optical probes PR1, PR2 made of a pair of optical fibers that are to be utilized in the NIRS measuring step S6 are mounted at the two marked positions as shown in FIG. 6(b). One of the optical probes is the optical probe PR1 for irradiating the near-infrared light and the other is the optical probe PR2 for detecting the near-infrared light diffused from the brain BR. In this embodiment, the optical probes PR1, PR2 are embedded into the headgear HC across a marker MK with an interval of approximately 2 cm, however, the positions where the optical probes PR1, PR2 are embedded can be determined by a physical position of the marker MK, a position or a shape of the activated portion AP of the brain BR, a positional relationship with other adjacent optical probes or a theoretical analysis result of brain optical propagation.

Figure 7:
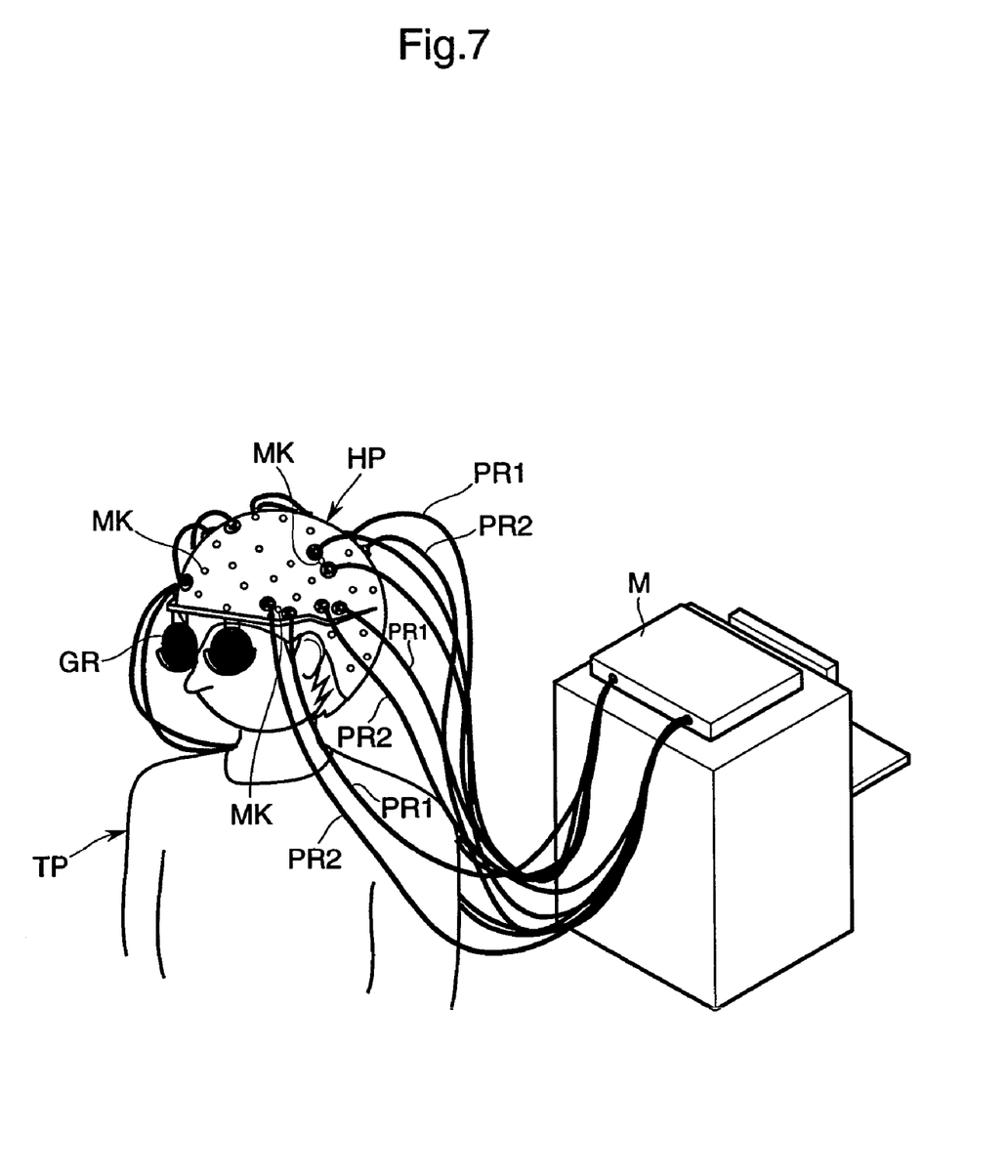
FIG. 7 is a view showing an NIRS measuring step in accordance with the embodiment.

In the NIRS measuring step S6, the headgear HC into which the optical probes PR1, PR2 have been embedded is put on the head portion of the subject TP by positioning the positioning portions HCp1, HCp2 with the nose and the ear of the subject TP and then the same stimulus as that of the fMRI measuring step S1 is given to the subject TP. More specifically in this embodiment, as mentioned above, the NIRS in the "binocular rivalry test" that monitors an activated state of the brain BR when different images are shown to each eye of the subject TP is conducted. In order to conduct the NIRS, the glasses GR shown in FIG. 7 are put on the subject TP and a pulse of infrared light is irradiated on the head portion of the subject TP through the optical probe PR1 for irradiation from a light source (omitted to show in drawings) of the NIRS measuring system M, the infrared light diffused from the brain BR is received through the optical probe PR2 for detection with the NIRS measuring system M and then a diachronic change in oxygenated hemoglobin (oxyHb) concentration and deoxygenated hemoglobin (deoxyHb) concentration of blood in a blood vessel of the brain BR of the subject TP is measured. The infrared light may be sampled at intervals of several tens of millisecond.

Figure 8:
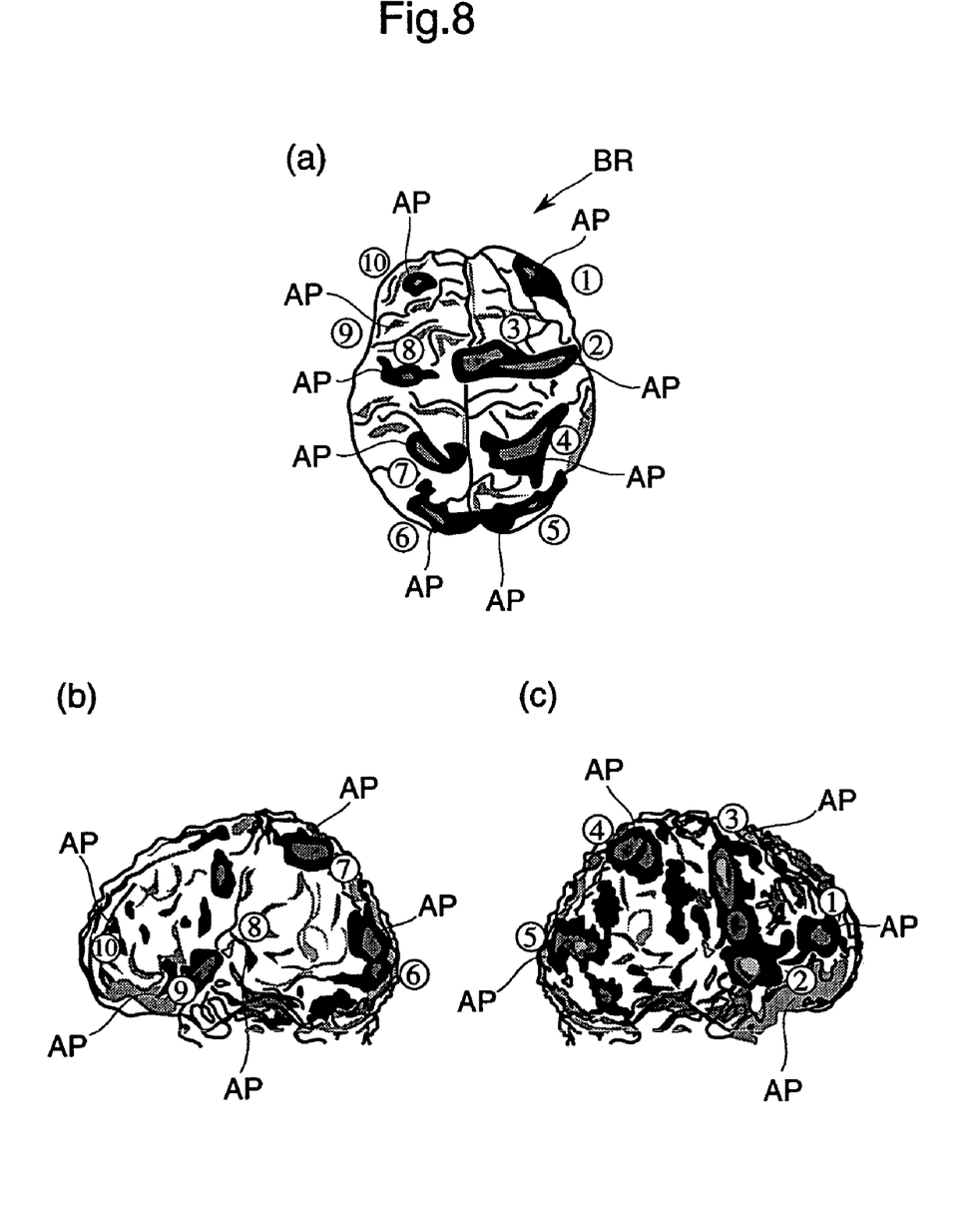
FIG. 8 is a view showing an activated portion of a brain in a binocular rivalry test in accordance with the embodiment.
Figure 9:
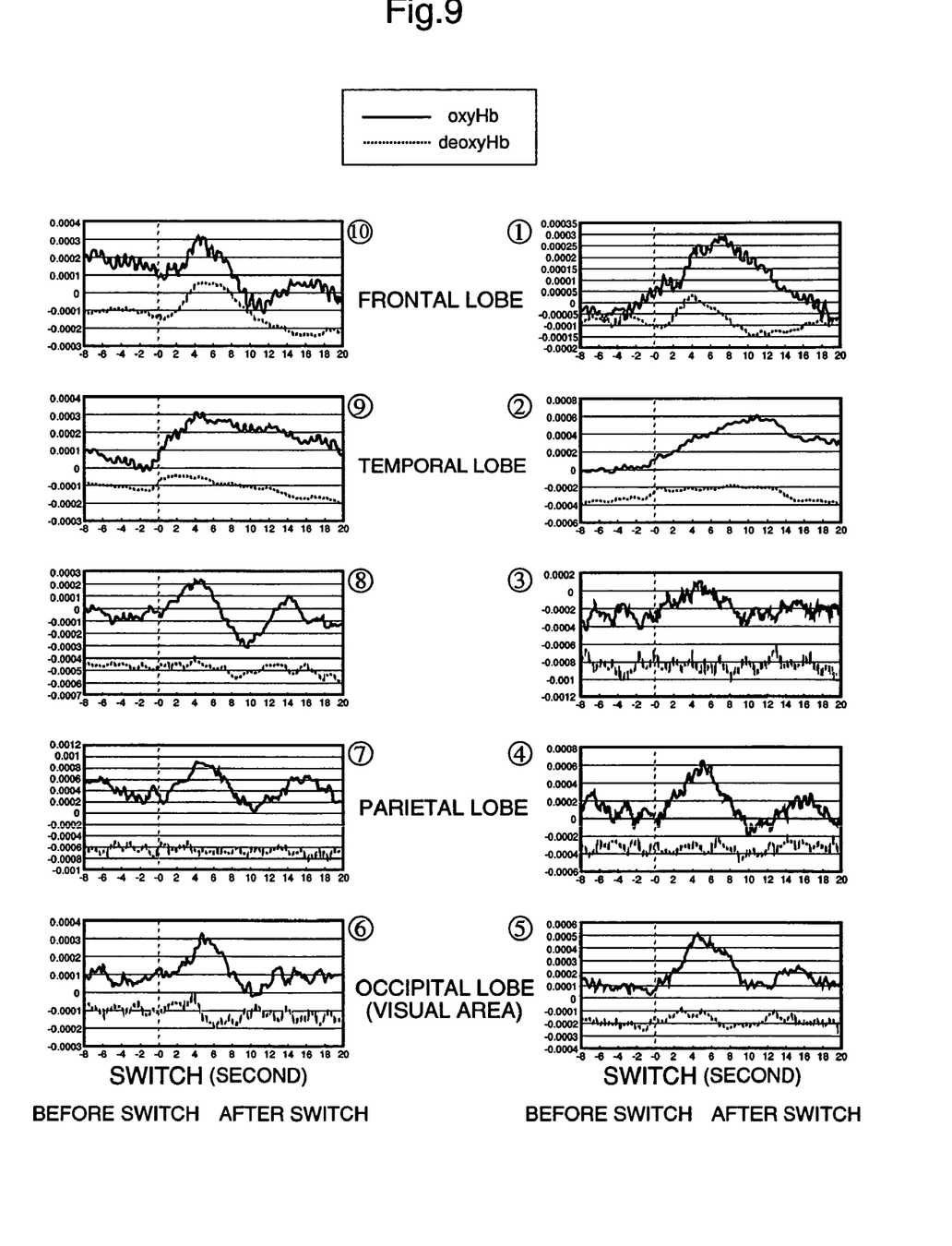
FIG. 9 is a view showing an NIRS measuring result in the binocular rivalry test to correspond to the activated portion of the brain.

FIG. 8 shows activated portions (1~10) of the brain BR of the subject TP based on the brain functional image IMGf wherein (a) is a plane view of the brain BR, (b) is a left side view of the brain BR and (c) is a right side view of the brain BR, and FIG. 9 shows a diachronic change (solid line) in oxygenated hemoglobin (oxyHb) concentration and a diachronic change (broken line) in deoxygenated hemoglobin (deoxyHb) concentration of each activated portion AP. When a stimulus was applied to the brain BR through the eyes in the binocular rivalry test, the oxygenated hemoglobin (oxyHb) concentration became higher at an activated portion of the brain BR (deep colored activated portion AP in FIG. 8). The result showed a high correlation between a result of the fMRI and a result of the NIRS. Since the high correlation was shown between the activated portion AP of the brain BR by the fMRI and hemoglobin (oxyHb, deoxyHb) concentration of blood in the brain BR by the NIRS, the method for mapping higher brain function in accordance with this embodiment makes it possible to map a higher brain function with a highly accurate space resolution and a highly accurate time resolution. As a result of this, this embodiment is a very useful method for mapping higher brain function.

The present claimed invention is not limited to the above-described embodiments and the concrete methods in each step may be variously modified without departing from the spirit of the invention.

As mentioned above, the present claimed invention is to obtain the brain functional image of the subject in advance by the fMRI, to manufacture the headgear to each subject, to obtain the head portion structural image with the MRI system in a condition that the subject puts the headgear on, to make a three-dimensionally combined image by combining the brain functional image and the head portion structural image three-dimensionally, to mount the optical probe at a portion of the heat gear near the activated portion of the brain determined by the brain functional image based on the three-dimensionally combined image and to conduct the MIRS measurement with the headgear put on. In accordance with the present claimed invention, the high space resolution based on the fMRI measurement and the high time resolution based on the NIRS measurement can be combined and the brain function at the activated portion of the brain activated by the stimulus can be mapped with an extremely high accuracy.

The invention claimed is:

1. A method for mapping higher brain function to map a higher brain function while a body of a subject is in a resting state or in a predetermined active state, comprising
an fMRI mapping step to map a brain function of the subject by functional magnetic resonance imaging,
a headgear mounting step to mount a headgear having markers on a head portion of the subject,
a head portion structural image acquisition step to acquire a head portion structural image of the subject having the mounted headgear by the magnetic resonance imaging,
a three-dimensional image combining step to create a three-dimensionally combined image showing the brain function and the head portion structure of the subject simultaneously by three-dimensionally combining the brain functional image obtained by the fMRI mapping step and the head portion structural image,
an optical probe mounting step to specify a position on the headgear where an optical probe that is used for near-infrared spectroscopy is mounted based on the three-dimensionally combined image and to mount the optical probe at the specified position, and
an NIRS measuring step to map the brain function of the subject by the near-infrared spectroscopy in a state that the headgear loaded with the optical probe is mounted on the head portion of the subject.

2. The method for mapping higher brain function described in claim 1 wherein during the optical probe mounting step, a marker corresponding to an activated portion of the brain determined based on the brain functional image included in the three-dimensionally combined image is specified from the markers on the headgear determined based on the head portion structural image included in the three-dimensionally combined image and an optical probe for irradiation of near-infrared light and an optical probe for detection of the near-infrared light diffused from the brain are mounted in pairs near the specified marker on the headgear.

3. The method for mapping higher brain function described in claim 2 further comprising a headgear manufacturing step prior to the headgear mounting step, wherein the headgear manufacturing step includes tailoring the headgear for the exclusive use of each subject.

4. The method for mapping higher brain function described in claim 2 wherein the optical probe for irradiation and the optical probe for detection are arranged apart by a predetermined distance across a corresponding marker.

5. The method for mapping higher brain function described in claim 4 further comprising a headgear manufacturing step prior to the headgear mounting step, wherein the headgear manufacturing step includes tailoring the headgear for the exclusive use of each subject.

6. The method for mapping higher brain function described in claim 4 wherein a distance between the optical probe for irradiation and the optical probe for detection or a direction of arranging the optical probe for irradiation and the optical probe for detection is determined based on a shape of the activated portion of the brain, a physical position of a headgear marker, a positional relationship with other adjacent optical probes or a theoretical analysis result of brain optical propagation.

7. The method for mapping higher brain function described in claim 6 further comprising a headgear manufacturing step prior to the headgear mounting step, wherein the headgear manufacturing step includes tailoring the headgear for the exclusive use of each subject.

8. The method for mapping higher brain function described in claim 1 further comprising a headgear manufacturing step prior to the headgear mounting step, wherein the headgear manufacturing step includes tailoring the headgear for exclusive use of each subject.

9. The method for mapping higher brain function described in claim 8 wherein during the headgear manufacturing step a plurality of the markers are evenly embedded at predetermined intervals into the headgear.

10. The method for mapping higher brain function described in claim 8 wherein during the headgear manufacturing step the head portion of the subject is covered with a flexible film, then a molding material is applied on the film in a flexible condition so as to make the headgear molded into a form of the head portion of the subject and the markers are embedded into the molding material before the molding material is cured.

* * * * *